United States Patent

Temmerman et al.

[11] Patent Number: 6,129,831
[45] Date of Patent: Oct. 10, 2000

[54] HYDROGEN PEROXIDE SENSOR

[75] Inventors: Eduard Temmerman, Wetteren; Philippe Westbroek, Zele; Paul Kiekens, Herzele, all of Belgium

[73] Assignee: Universiteit Gent - Vakgroep Textielkunde, Zwijnaarde, Belgium

[21] Appl. No.: 08/923,987

[22] Filed: Sep. 5, 1997

Related U.S. Application Data

[63] Continuation-in-part of application No. PCT/BE96/00006, Jan. 23, 1996.

[30] Foreign Application Priority Data

Jan. 26, 1995 [BE] Belgium ............................ 959500063

[51] Int. Cl.$^7$ ............................ G01N 27/30; G01N 27/26
[52] U.S. Cl. ........................ 205/775; 205/780; 205/782; 205/786; 204/294; 204/412
[58] Field of Search .................................. 205/775, 780, 205/782, 786; 204/294, 412

[56] References Cited

U.S. PATENT DOCUMENTS 5,364,510  11/1994  Carpio .................................. 204/153.1

FOREIGN PATENT DOCUMENTS

WO9118296  11/1991  WIPO .

OTHER PUBLICATIONS

Journal of Electroanalytical Chemistry, vol. 205, No. 1, Lausanne, pp. 63–71, XP002002264, K. Aoki et al Electronic Kinetics of the Oxidation . . . Carbon Fiber Electrodes (no month).

Patent Abstracts of Japan, vol. 009, No. 217 (P–385), Sep. 4, 1985 & JP A 60 07661 (Nihon Bunkou Kogyo KK), May 1, 1985.

Analytical Chemistry, vol. 50, No. 7, Columbus, US, pp. 933–936, XP002002265, W.J. Blaedel; G.A. Mabbott: Pyrolytic Carbon Film Electrode (no month).

Database WPI Section CH, Week 7907, Derwent Publications, Ltd. London, GB, Class E36, An 79–13918B XP002002266, Pisaerevskii: "Hydrogen perixode potential . . . with Graphite" (no month).

Patent Abstracts of Japan, vol. 015, No. 312 (P–1236), Aug. 9, 1991 & JP A 03 113360 (Tekunoroogu:KK) May 14, 1991.

Patent Abstracts of Japan, vol. 008, No. 121, (P–278), Jun. 7, 1984 & JP A 59 026049 (Denki Kagaku Keiki KK), Feb. 10, 1984.

*Primary Examiner*—Deborah Jones
*Assistant Examiner*—Jennifer C. McNeil
*Attorney, Agent, or Firm*—Sughrue, Mion, Zinn, Macpeak & Seas, PLLC

[57] ABSTRACT

The sensor electrode has a sensing surface intended to contact a liquid medium for continuous measuring, in combination with a counter electrode and a reference electrode, of the hydrogen peroxide concentration over a concentration range from 0.005 mole/liter to 3 mole/liter, said sensor consisting of a carbon electrode having an open circuit potential between –65 and –85 mV, said open circuit potential being measured with respect to a Ag/AgCl/saturated Cl$^-$ reference electrode in an alkaline solution having a pH between 10.5 and 14, said solution containing hydrogen peroxide at a concentration of more than 0.5 mole/liter.

20 Claims, 4 Drawing Sheets

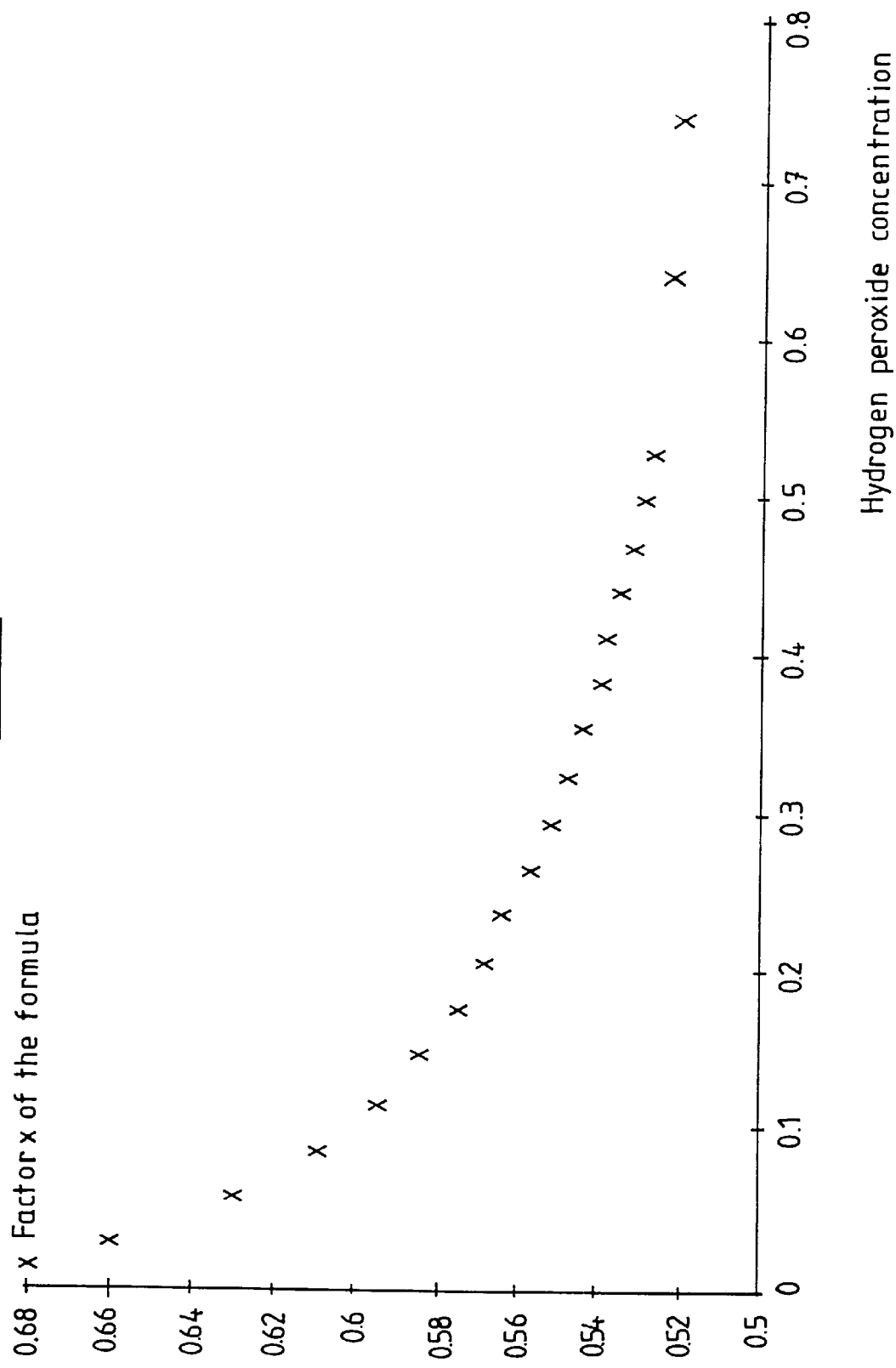

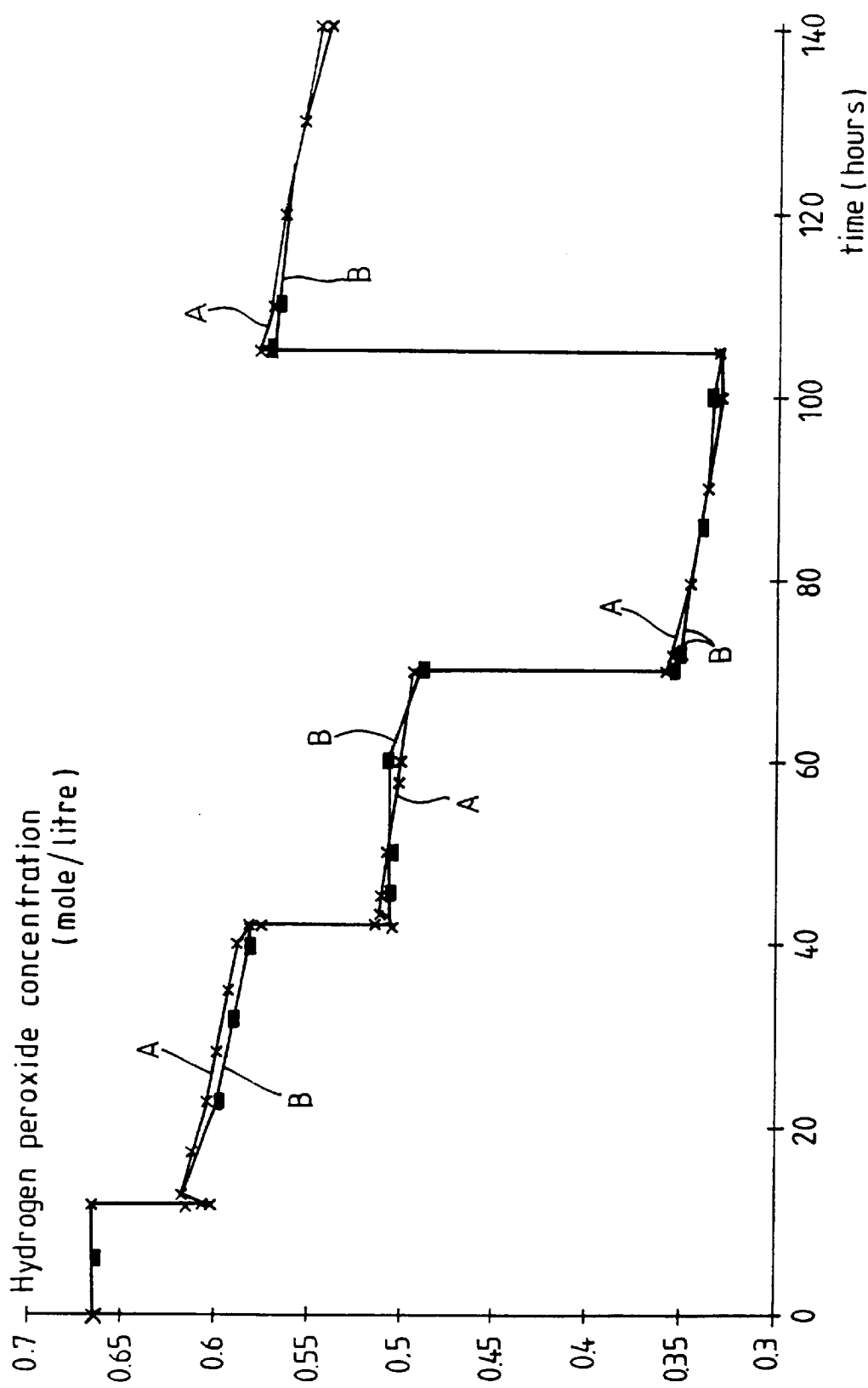

HYDROGEN PEROXIDE SENSOR

This is a Continuation-in-Part of International Application No. PCT/BE96/0006 filed Jan. 23, 1996 designating the U.S.

THE PRIOR ART

Until now, it has not been possible satisfactorily to monitor the hydrogen peroxide concentration in a continuous and automated way.

A number of techniques are available for measuring the hydrogen peroxide concentration of a solution. These techniques do not offer satisfaction due to interference and too long response times.

It is very important in some applications, such as when treating sewage water, to have an accurate and quick measurement of the hydrogen peroxide concentration. For some applications, such as bleaching operations, it is important to keep the hydrogen peroxide concentration constant, which requires an accurate and fast measurement of the hydrogen peroxide concentration.

The most commonly applied technique for the determination of the hydrogen peroxide concentration consists of a redox titration with potassium permanganate in an acidic medium. The purple permanganate ion is reduced to manganese (II), while hydrogen peroxide is oxidised to oxygen. This titration may be carried out by a worker who is often responsible for other tasks as well. Purchasing an automatic titration system is often too expensive and the response time with this technique is also more than ten minutes. Besides these important drawbacks, human errors may occur such as misinterpretation of titration data which entails faulty concentration measurement. Also, reagents such as potassium permanganate and sulphuric acid need to be used. The invention aims at a sensor that can monitor the hydrogen peroxide concentration in a direct way without the need of sampling and without using potassium permanganate, sulphuric acid or any other chemicals.

A second technique which does enable continuous monitoring of hydrogen peroxide is based on FIA (Flow Injection Analysis) techniques and colorimetry. They are described by Jola in Melliand Textilberichte 11 (1980) p. 931–936.

Solution is drawn off at constant flow rate and pumped through a by-pass. The solution is diluted with distilled water via a vessel. The flow rate of this water is constant too. This dilution is necessary to come within the range of validity of the law of Bouger-Lambert-Beer. Finally, a colour reagent which reacts with hydrogen peroxide is added, also with a constant flow rate. In the spectrophotometer, the absorption at the corresponding wavelength, which is proportional to the hydrogen peroxide concentration, is then measured. Although this technique allows continuous monitoring, it has a number of shortcomings. Other particles in the solution may interfere by reacting with the colour reagent. Insoluble particles such as fibre particles may affect absorption as well. Continuous measurement of the hydrogen peroxide concentration by means of the FIA-technique is based on the constant flow rate being maintained in the pump pipes. The by-pass pipes however can narrow down because of solid deposition from the solution to be measured, which irrevocably gives rise to faulty conclusions. The major drawback however is the high cost of the technique.

Finally, other techniques have been developed which are based on conductometry in combination with temperature and pH measurement. Sensitivity and specificity of these techniques are not discussed here and the techniques are inappropriate.

The sensor electrode according to the invention is based on the application of a voltammetric reaction at the surface of a carbon electrode, the current of said reaction being proportional to the hydrogen peroxide concentration.

Several types of carbon may be used such as graphite, pyrolytic graphite, glassy carbon, etc. In spite of the higher price, glassy carbon is preferred because of its high inertness, high hardness and hence good resistance to erosion by the measurement solution and because of its high stability at prolonged application of a potential.

However, in order to have a good performance of the sensor, the carbon electrode needs to have an appropriate open circuit potential, namely a stable open circuit potential between −65 and −85 mV, said open circuit potential being measured in an alkaline solution having a pH between 10.5 and 14, and a hydrogen peroxide concentration of more than 0.5 mole/liter and this with respect to a Ag/AgCl/saturated Cl$^-$ reference electrode.

An untreated carbon electrode has no stable open circuit potential. The carbon electrode with a sensing surface polished by means of sandpaper has an open circuit potential of about −95 mV, while said carbon electrode after polishing the sensing surface successively with $Al_2O_3$ polishing powder with a grit larger than 0.3 μm, and with $Al_2O_3$ polishing powder with a grit diameter smaller than 0.3 μm, has an open circuit potential of about −140 mV, said open circuit potentials being, measured in an alkaline solution having a pH between 10.5 and 14, and a hydrogen peroxide concentration of more than 0.5 mole/liter and this with respect to a Ag/AgCl/saturated Cl$^-$ reference electrode.

Moreover, said carbon electrodes have a low stability, i.e. the open circuit potential of the carbon electrodes fluctuates more than 5 mV with respect to their mean open circuit potential.

BRIEF DESCRIPTION OF THE INVENTION

The invention relates to a sensor electrode for continuously measuring a hydrogen peroxide concentration over a ranging from 0.005 mole/liter to 3 mole/liter. The sensor electrode has a sensing surface for contacting a liquid medium. The sensor consists of a carbon electrode having an open circuit potential between −65 and −85 mV, mostly around −72 mV, the fluctuation margin of the open circuit potential of the sensor electrode, once established, being less than 2 mV with respect to the mean open circuit potential. The said open circuit potential is measured in an alkaline solution having a pH between 10.5 and 14, and a hydrogen peroxide concentration of more than 0.5 mole/liter and this with respect to a Ag/AgCl/saturated Cl$^-$ reference electrode.

The said sensing surface is subjected to the following treatments:

(a) mechanically polishing the sensing surface successively with sandpaper, with $Al_2O_3$ polishing powder with a grit larger than 0.3 μm, and with $Al_2O_3$ polishing powder with a grit diameter smaller than 0.3 μm;

(b) cleaning by ultrasonic vibration;

(c) a first electrochemical treatment of the sensor electrode in an aqueous solution having a pH between 10.5 and 14 and a hydrogen peroxide concentration of more than 0.5 mole/liter, a water decomposition potential by reduction and a water decomposition potential by oxidation, the sensing surface being subjected to successive cycles of sweeping potential between a first potential more negative than the said water decomposition potential by reduction and a second potential more positive than the water decomposition potential by oxidation, whereby each cycle is characterised by a current-potential curve, said first electrochemical treatment being continued until a difference of less then 1% is obtained between all data points of the current-potential curves of two successive cycles of sweeping the potential between the said first potential and the said second potential;

(d) a second electrochemical treatment of the sensor electrode in an aqueous solution having a pH between 10.5 and 14 and a hydrogen peroxide concentration of more than 0.5 mole/liter, said second electrochemical treatment consisting of maintaining between the sensor electrode and the reference electrode a constant potential difference of +0.54V until an open circuit potential of between −65 mV and −85 mV is measured for the sensor electrode. The open circuit potential is measured in an alkaline solution having a pH between 10.5 and 14 and having a hydrogen peroxide concentration of more than 0.5 mole/liter, and this with respect to a Ag/AgCl/saturated Cl⁻ reference electrode.

The invention also relates to a system for continuous measurement of the hydrogen peroxide concentration in a range of concentrations from 0.005 mole/liter to 3 mole/liter of a solution having a pH higher than 10.5. The said system comprises:

(a) a carbon sensor electrode having a sensing surface for contacting a liquid medium, said sensor consisting of a carbon electrode having an open circuit potential between −65 and −85 mV, the fluctuation margin of the open circuit potential of the sensor electrode, once established being less than 2 mV with respect to the mean open circuit potential, said open circuit potential being measured in an alkaline solution having a pH between 10.5 and 14, and a hydrogen peroxide concentration of more than 0.5 mole/liter, and this with respect to a Ag/AgCl/saturated Cl⁻ reference electrode;

(b) a counter electrode;

(c) a reference electrode;

(d) a temperature sensor and/or a system controlling and adjusting the temperature of the liquid medium;

(e) a sensor, the output of which is function of the OH⁻ concentration of the liquid medium, and/or a system for controlling and adjusting the pH of the liquid medium, and (f) an electronic device connected to the sensor electrode, the counter electrode, the reference electrode, the temperature sensor and the sensor, the output of which is function of the OH⁻ concentration of the liquid medium, said electronic device calculating the hydrogen peroxide concentration by means of the following formula (or a formula derived from said formula when temperature and/or pH are maintained constant by one of said controlling systems or by both controlling systems):

$$c_{per} = \left[ c_{per,cal}^{(1.5x_{cal}-0.5)} \frac{I_m}{I_{cal}} \frac{c_{OH_{cal}}^{(1.5-0.5x_{cal})}}{c_{OH_m}^{(1.5-0.5x_m)}} e^{0.03049(T_{cal}-T_m)} \right]^{\frac{1}{(1.5x_m-0.5)}}$$

in which $c_{OH_{cal}}$, $T_{cal}$, $c_{per,cal}$ and $I_{cal}$ are respectively the OH⁻ concentration of the solution used for the calibration of the sensor electrode, the temperature of the solution used for the calibration of the sensor electrode, the hydrogen peroxide concentration of the solution used for calibration of the sensor and the output of the sensor electrode in the solution used for calibration;

$T_m$ is the temperature of the solution of which the hydrogen peroxide concentration is to be measured;

$c_{OH_m}$ is the OH⁻ concentration of the solution of which the hydrogen peroxide concentration is to be measured, $I_m$ is the output of the sensor electrode in the solution of which the hydrogen peroxide concentration is to be measured;

$x_{cal}$ and $x_m$ are equal to about 0.53 for the determination of hydrogen peroxide concentrations higher than 0.5 mole/liter or are calculated by a specific formula for hydrogen peroxide concentrations lower than 0.5 mole/liter, and $c_{per}$ is the hydrogen peroxide concentration in the solution of which the hydrogen peroxide concentration is to be measured.

In a special setup suitable for industry, the sensor electrode is mounted in a by-pass. The system can be provided with a pump for pumping solution through the by-pass.

At sufficient flow rate in the by-pass, stationary flow condition can be reached in the solution. With such a stationary flow condition, the output of the carbon electrode is stable, which is an absolute condition for the technique to be applied in a continuous way.

The reference electrode is advantageously a Ag/AgCl/saturated Cl⁻ electrode, though other types of reference electrodes may also be used on the condition that the reference electrode can obtain a stable potential in the solution.

The counter electrode used in the system is for example a graphite rod or any other inert material that conducts electric current.

In a possible application of the invention, the sensor electrode is mounted in a by-pass which is connected to the bath in which hydrogen peroxide concentration has to be monitored.

These features and other features and details of the invention will become apparent from the description given below, with reference to the accompanying figures, which show a realisation of the invention by way of example and not in a constraining sense.

BRIEF DESCRIPTION OF THE DRAWINGS

In the attached drawings:

FIG. 6 is a graph showing the variation of the factor "x" in the formula used in the electronic means of the system of the invention, and FIG. 7 is a graph showing the hydrogen peroxide concentration of a solution as calculated by the results of titration with potassium permanganate (curve A) and the hydrogen peroxide concentration measured on a continuous way by a by-pass system of the invention (curve B).

DESCRIPTION OF THE INVENTION

Figure 1:
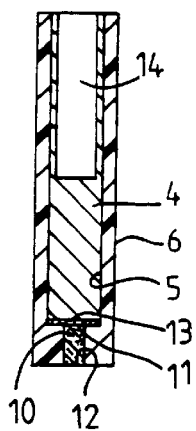
FIG. 1 is a schematic representation of a sensor electrode according to the invention.
Figure 4:
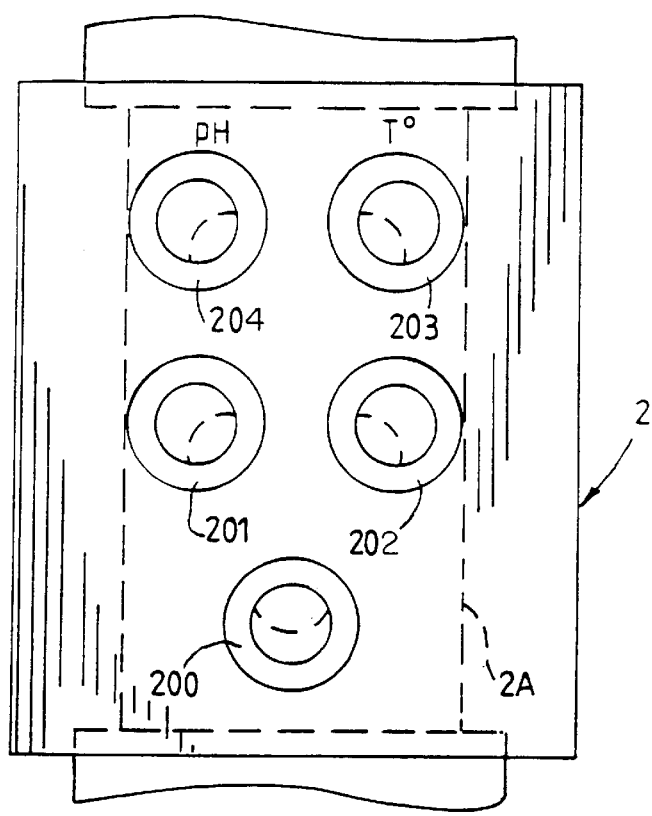
FIGS. 3 and 4 are perspective view and view from above of the system used in FIG. 2.
Figure 3:
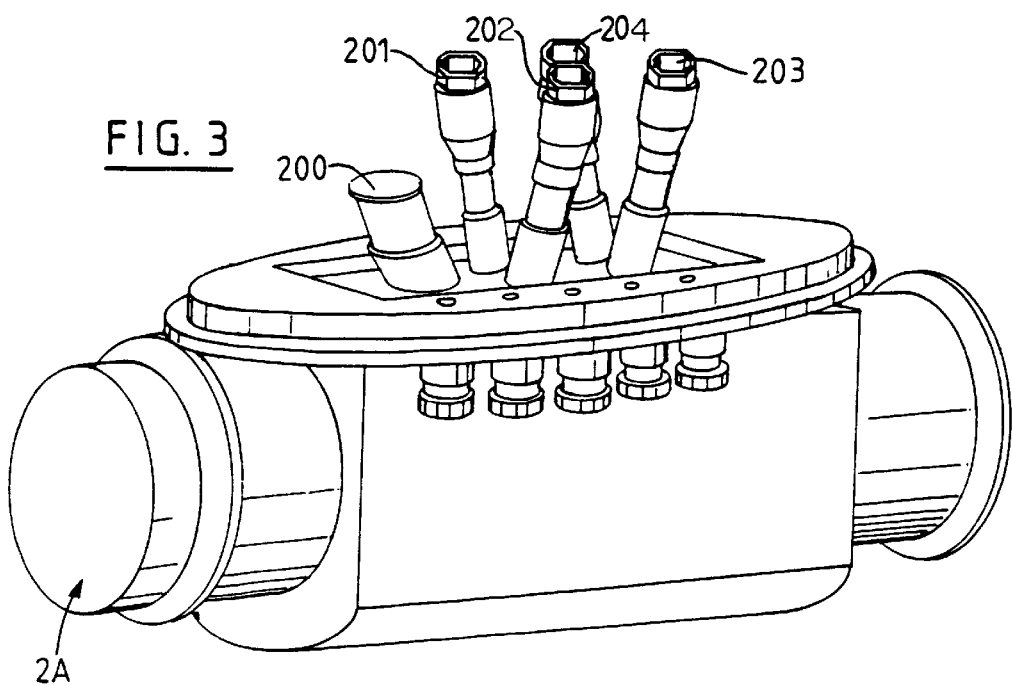

The sensor electrode of the invention shown in FIG. 1 comprises a carbon element 10 having a cylindrical shape. Said carbon element 10 extends between a first end 11 and a second end 12, the first end contacting a copper base 4 via the interposition of a conductive layer 13, such as a layer of silver particles. Said copper base 4 and the carbon element 10 are embedded in an epoxy resin envelope 6 so that the second end 12 of the carbon element is free of resin. The copper base 4 is provided, on its face opposite to the face adjacent to the carbon element 10, with an opening 14 adapted for receiving a plug of a connecting means. The second end of the carbon element is the sensing surface 12 intended to contact the liquid medium. The said sensor electrode is a carbon electrode having an open circuit potential between −65 and −85 mV, mostly around −72 mV, the fluctuation margin of the open circuit potential of any individual sensor electrode, once established, being less than 2 mV with respect to the mean open circuit potential. The said open circuit potential is measured in an alkaline solution having a pH between 10.5 and 14, and having a hydrogen peroxide concentration of more than 0.5 mole/liter, and this with respect to a Ag/AgCl/saturated Cl⁻ reference electrode. Said measurement was carried out at a temperature of 20±5° C.

Such a sensor electrode is for example manufactured as follows:

STEP 1: A glassy carbon rod is attached to a copper base via an epoxy layer containing silver particles, said copper base and carbon rod being thereafter embedded in an epoxy resin.

STEP 2: The second end of the carbon rod or sensing surface of the electrode is mechanically treated or polished successively with sandpaper (for example SiC-emery paper), with $Al_2O_3$ polishing powder with a grit diameter of 1 μm (for 10 minutes), with $Al_2O_3$ polishing powder with a grit diameter of 0.3 μm (for 15 minutes) and with $Al_2O_3$ polishing powder with a grit diameter of 0.05 μm (for 20 minutes). The mechanical treatment using polishing powder is done by pushing the sensing surface on a rotating wet disc covered with cloth on which the polishing powder has been placed.

STEP 3: The sensing surface is cleaned by ultrasonic vibration in an aqueous bath for removing the remaining polishing particles from the sensing surface.

STEP 4: The sensing surface is submitted to a first electrochemical treatment by applying a potential scan in an aqueous solution having a pH between 10.5 and 14 (for example 12.5), a hydrogen peroxide concentration of more than 0.5 mole/liter (for example 0.55 mole/liter) and a temperature from 0° C. to the boiling point (for example 25° C.). Temperatures higher than 100° C. are possible when such treatment is done in a closed vessel or autoclave, the pressure of which is for example higher than $1.5 \cdot 10^5$ Pa. Said solution has a water decomposition potential by reduction and a water decomposition potential by oxidation. The sensing surface is subjected to successive cycles of sweeping its potential between a first potential more negative (for example a potential of −1.7V) than the said water decomposition potential by reduction and a second potential more positive (for example a potential of 1V) than the water decomposition potential by oxidation. Each cycle is characterised by a current-potential curve, said first electrochemical treatment being continued until a difference of less then 1% between all data points of the current-potential curves of two successive cycles of sweeping the potential between the said first potential and the said second potential. The rate of potential variation between −1.7V and 1V was in this example about 25 mV/s.

STEP 5: The sensing surface is then submitted to a second electrochemical treatment in an aqueous solution having a pH between 10.5 and 14 (for example 12.5) and a hydrogen peroxide concentration of more than 0.5 mole/liter (for example 0.55). The said second electrochemical treatment consists of maintaining between the sensor electrode and the reference electrode a constant potential difference of +0.54V for a period of 3 hours at 80° C. (10 hours at 50° C., less then 3 hours at a temperature higher than 80° C.) until an open circuit potential of −72±2 mV is measured for the sensor electrode in an alkaline solution having a pH of 12.5, a temperature of 25° C. and a hydrogen peroxide concentration of 0.55 mole/liter, and this with respect to a Ag/AgCl/saturated Cl⁻ reference electrode.

The open circuit potential of several electrodes was measured in an alkaline solution having a pH of 12.5, a temperature of 25° C. and containing hydrogen peroxide at a concentration of 0.55 mole/liter, and this with respect to a Ag/AgCl/saturated Cl⁻ reference electrode.

For the carbon electrode after polishing with SiC emery paper, the open circuit potential was about −95 mV. For the electrode obtained at the end of STEP 2, the open circuit potential was equal to about −140 mV. After the first electrochemical treatment (STEP 4), the open circuit potential was equal to about −45 mV. After 5 hours of the second electrochemical treatment at 50° C., the open circuit potential was not stable and equal to about −60 mV. After full treatment, the open circuit potential was equal to −72 mV, the fluctuation margin of this open circuit potential of the latter electrode, once established, being less than 2 mV with respect to the mean open circuit potential. It means that when making successive measurements of the open circuit potential, the value obtained from said successive measurements remains substantially constant, i.e. that the electrode was very stable. The potential fluctuations for the electrodes not fully treated were 10 to 15 mV, i.e. the electrodes that are not fully treated are more unstable.

Figure 2:
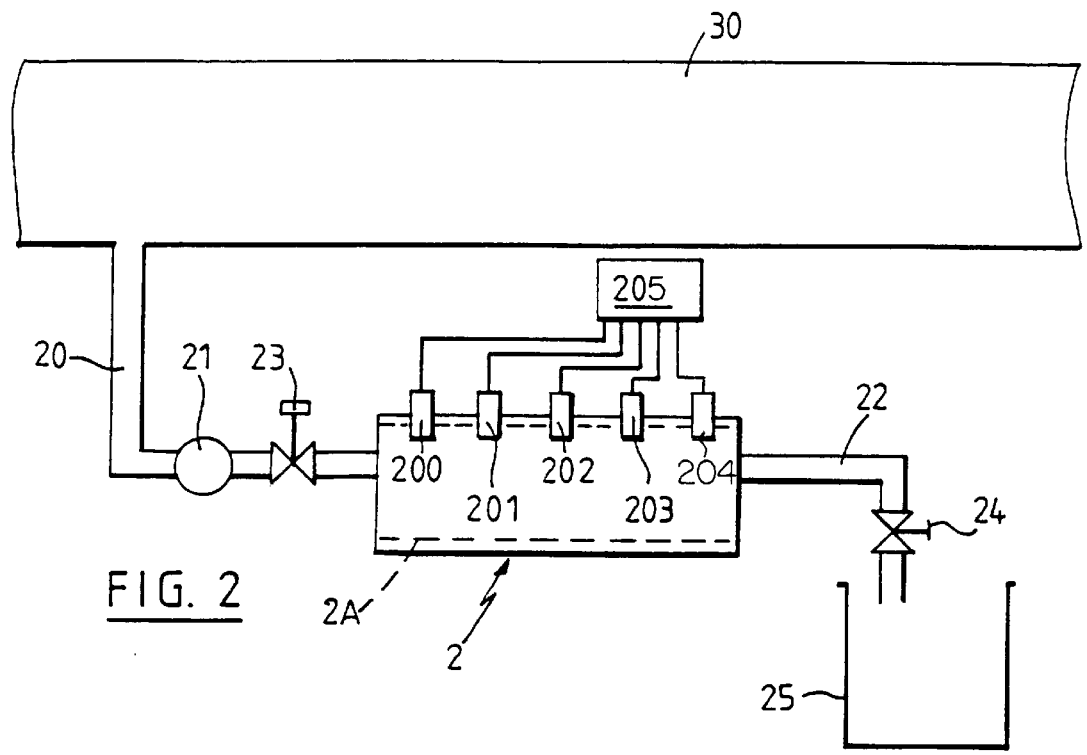
FIG. 2 is a schematic representation of an embodiment of a system of the invention in a by-pass configuration (cross section of the by-pass tube)

FIG. 2 shows a system 2 according to the invention mounted on a by-pass pipe 20 of a bleaching unit comprising a pipe 30 in which the bleaching solution flows. A pump 21 is mounted on the pipe 20 so as to convey a part of the bleaching solution into the system 2, a pipe 22 conducting the bleaching agent escaping from the system into a container 25. Valves 23, 24 are provided on the pipes 20 and 22 so as to control the flow of bleaching solution in the system 2. Said system 2 comprises:

(a) a sensor electrode 200 having a sensing surface intended to contact the liquid medium, said sensor electrode consisting of a carbon electrode having an open circuit potential between −65 and −85 mV, the fluctuation margin of the open circuit potential the sensor electrode, once established, being less than 2 mV with respect to the mean open circuit potential, said open circuit potential being measured in an alkaline solution having a pH between 10.5 and 14, said solution having a hydrogen peroxide concentration of more than 0.5 mole/liter, and this with respect to a Ag/AgCl/saturated Cl⁻ reference electrode;

(b) a counter electrode 201, such as a platinum, carbon or stainless steel electrode;

(c) a reference electrode 202, such as a Ag/AgCl/saturated Cl⁻ reference electrode;

(d) a temperature sensor 203;

(e) a second sensor 204 such as a glass electrode, the output of which is function of the OH⁻ concentration of the solution, or a system for measuring and controlling the pH of the solution;

(f) a sensing pipe 2A defining the volume in which the sensing operation takes place, and (g) an electronic device 205 (with potentiometric circuit) connected to the sensor electrode 200, the counter electrode 201, the reference electrode 202, the temperature sensor 203 and the second sensor 204, the output of which is function of the OH⁻ concentration of the solution. For the measurement of a hydrogen peroxide concentration ranging from 0.5 mole/liter to 3 mole/liter, said electronic device calculates the hydrogen peroxide concentration by means of the following formula (or a formula derived from said formula when temperature and/or pH are maintained constant):

$$c_{per} = \left[ c_{per,cal}^{(1.5x_{cal}-0.5)} \frac{I_m}{I_{cal}} \frac{c_{OH^-_{cal}}^{(1.5-0.5x_{cal})}}{c_{OH^-_m}^{(1.5-0.5x_m)}} e^{0.03049(T_{cal}-T_m)} \right]^{\frac{1}{(1.5x_m-0.5)}}$$

in which $c_{OH^-cal}$, $T_{cal}$, $c_{per,cal}$ and $I_{cal}$ are respectively the OH⁻ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ concentration of the solution of which the hydrogen peroxide concentration is to be measured;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

When the system is intended to measure hydrogen peroxide concentrations smaller than 0.5 mole/liter in a solution having a pH higher than 10.5, the electronic device makes use of the following relationship between the factor x and the hydrogen peroxide concentration:

$$x = k \cdot c_{per}^y$$

in which x is the x factor, k and y are constants and equal to k=0.6664 and y=−0.08055;

$c_{per}$ is the hydrogen peroxide concentration.

Inserting the said formula into the overall formula used by the electronic device the hydrogen peroxide concentration is obtained by iterations by means of the following formula:

$$c_{per} = \left[ c_{per,cal}^{(1.5(kc_{per,cal}^y)-0.5)} \frac{I_m}{I_{cal}} \frac{c_{OH^-_{cal}}^{(1.5-0.5(kc_{per,cal}^y))}}{c_{OH^-_m}^{(1.5-0.5(kc_{per}^y))}} e^{0.03049(T_{cal}-T_m)} \right]^{\frac{1}{(1.5(kc_{per}^y)-0.5)}}$$

in which $c_{OH^-cal}$, $T_{cal}$, $c_{per,cal}$ and $I_{cal}$ are respectively the OH⁻ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the OH⁻ concentration of the solution of which the hydrogen peroxide concentration is to be measured;

$I_m$ is the output of the sensor electrode in the solution of which the hydrogen peroxide concentration is to be measured;

k and y are constant values;

$c_{per}$ is the hydrogen peroxide concentration of the solution of which the hydrogen peroxide concentration is to be measured.

After inserting all said elements except $c_{per}$ into the said equation, each iteration comprises the following steps:

STEP A: Inserting an estimated hydrogen peroxide concentration $c_{per}(t_r)$ into the said formula;

STEP B: Calculating by means of said formula a calculated hydrogen peroxide concentration;

STEP C: Calculating the difference between the calculated hydrogen peroxide concentration $c_{per}(t_l)$ and the estimated hydrogen peroxide concentration: $c_{per}(t_l)-c_{per}(t_r)$ STEP D: Calculating a new input for the estimated concentration of hydrogen peroxide, for example taking into account the difference calculated in STEP C $$c_{per,new} = c_{per}(t_l) - ((c_{per}(t_l) - c_{per}(t_r))/2)$$

said steps B–C–D being repeated until $c_{per}(t_l)$ is equal or substantially equal to $c_{per}(t_r)$ or until the difference is within a predetermined accuracy range, for example a range of −1% of $c_{per}(t_l)$ to 1% of $c_{per}(t_l)$.

Figure 5:
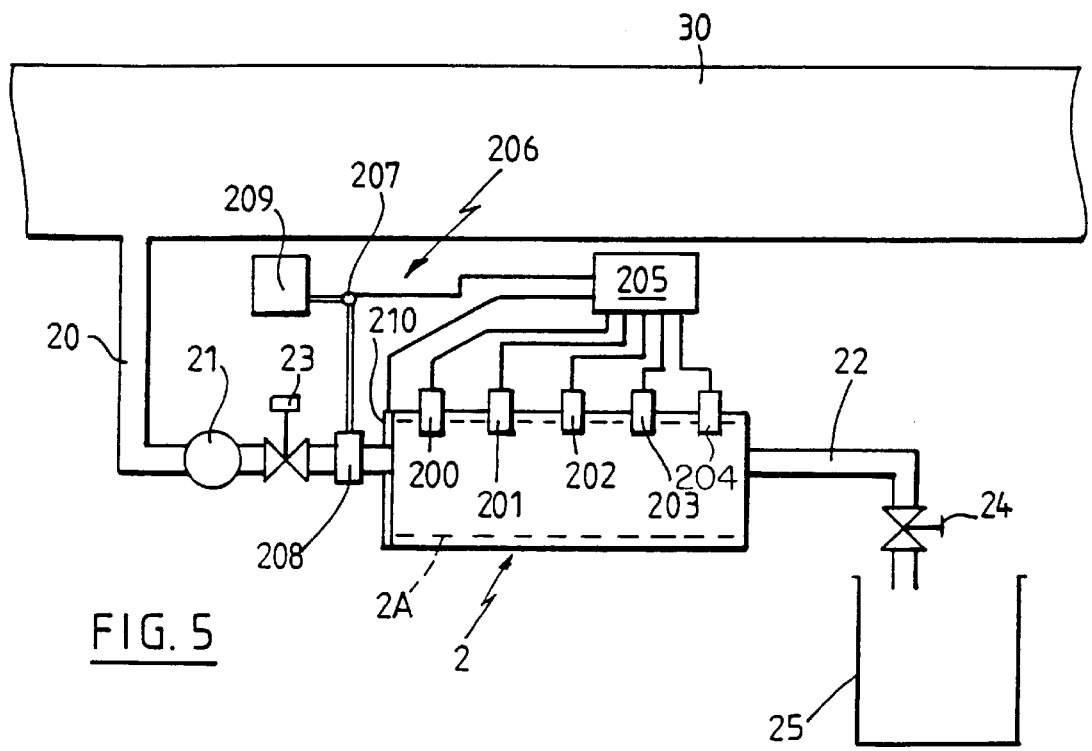
FIG. 5 is a schematic representation of a specific system according to the invention implemented at the by-pass tube of a process machine.

The system of FIG. 5 is similar to the system of FIG. 2 except that the system is further provided with:

a temperature regulating system 210 for controlling and adjusting the temperature of the solution of which the hydrogen peroxide concentration is to be measured (preferably to about a specific predetermined temperature comprised between 20 and 80° C.), said system being controlled by the electronic device 205; and a system 206 for controlling and adjusting the pH of the solution passing through the system 2 at a value of at least 10.5 (for example 12.5), said system comprising a container 209 containing a strongly alkaline solution and a pump 207 for injecting said alkaline solution in a mixing vessel 208 situated on the pipe 20, the said pump being controlled by the electronic device 205.

When the temperature regulating system is operated and the temperature is kept constant, the device 205 calculates the hydrogen peroxide concentration in a range of hydrogen peroxide concentration from 0.5 mole/liter to 3 mole/liter of a solution having a pH higher than 10.5 as follows if the system is calibrated at the said constant value of the temperature, by means of the following formula:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} \right]^{\frac{1}{(1.5x_m-0.5)}}$$

in which $c_{OH^-cal}$, $c_{per,cal}$ and $I_{cal}$ are respectively the OH$^-$ concentration of the solution used for the calibration of the sensor electrode, the hydrogen peroxide concentration of the solution used for the calibration of the sensor electrode and the output of the sensor electrode in the solution used for calibration;

$c_{OH^-m}$ is the OH$^-$ concentration of the solution of which the hydrogen peroxide concentration is to be measured;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

If the temperature is kept constant by the temperature controlling system and if the sensor electrode is not calibrated at said constant value of the temperature, then the hydrogen peroxide concentration is calculated by means of the following formula:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

in which $c_{OH^-cal}$, $T_{cal}$, $c_{per,cal}$ and $I_{cal}$ are respectively the OH$^-$ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the OH$^-$ concentration of the solution of which the hydrogen peroxide concentration is to be measured;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

When the system is intended to measure hydrogen peroxide concentrations smaller than 0.5 mole/liter in a solution having a pH higher than 10.5, the electronic device makes use of the following relationship between the factor x and the hydrogen peroxide concentration:

$$x = k \cdot c_{per}^y$$

in which x is the x factor;

k and y are constants and equal to k=0.6664 and y=−0.08055;

$c_{per}$ is the hydrogen peroxide concentration.

Inserting the said formula into the overall formula used by the electronic device, the hydrogen peroxide concentration is obtained by iterations by means of the following formula:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} \right]^{\frac{1}{(1.5(kc_{per}^y)-0.5)}}$$

in which $c_{OH^-cal}$, $c_{per,cal}$ and $I_{cal}$ are respectively the OH$^-$ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$c_{OH^-m}$ is the OH$^-$ concentration of the solution of which the hydrogen peroxide concentration is to be measured;

$I_m$ is the output of the sensor electrode in the solution of which the hydrogen peroxide concentration is to be measured;

k and y are constant values $c_{per}$ is the hydrogen peroxide concentration of the solution of which the hydrogen peroxide concentration is to be measured.

After inserting all said elements except $c_{per}$ into the said equation, each iteration comprises the following steps:

STEP A: Inserting an estimated hydrogen peroxide concentration $c_{per}(t_r)$ into the said formula;

STEP B: Calculating by means of said formula a calculated hydrogen peroxide concentration $c_{per}(t_l)$;

STEP C: Calculating the difference between the calculated hydrogen peroxide concentration $c_{per}(t_l)$ and the estimated hydrogen peroxide concentration: $c_{per}(t_l) - c_{per}(t_r)$ STEP D: Calculating a new input for the estimated concentration of hydrogen peroxide, for example taking into account the difference calculated in STEP C $$c_{per,new} = c_{per}(t_l) - ((c_{per}(t_l) - c_{per}(t_r))/2)$$

said steps B–C–D being repeated until $c_{per}(t_l)$ is equal or substantially equal $c_{per}(t_r)$ or until the difference is within a predetermined accuracy range, for example a range of −10% of $c_{per}(t_l)$ to 1% of $c_{per}(t_l)$.

When the system is intended to measure hydrogen peroxide concentrations smaller than 0.5 mole/liter in a solution having a pH higher than 10.5, if the temperature is kept constant by controlling said parameter and if the sensor electrode is not calibrated at said constant value of the temperature, then the hydrogen peroxide concentration is calculated by means of the following formula:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y)-0.5)}}$$

in which $c_{OH^-cal}$, $T_{cal}$, $c_{per,cal}$ are respectively the OH$^-$ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the $OH^-$ concentration of the solution of which the hydrogen peroxide concentration is to be measured;

$I_m$ is the output of the sensor electrode in the solution of which the hydrogen peroxide concentration is to be measured;

k and y are constant values $c_{per}$ is the hydrogen peroxide concentration of the solution of which the hydrogen peroxide concentration is to be measured.

After inserting all said elements except $c_{per}$ into the said equation, each iteration comprises the following steps:

STEP A: Inserting an estimated hydrogen peroxide concentration $c_{per}(t_r)$ into the said formula, STEP B: Calculating by means of said formula a calculated hydrogen peroxide concentration $c_{per}(t_l)$;

STEP C: Calculating the difference between the calculated hydrogen peroxide concentration $c_{per}(t_l)$ and the estimated hydrogen peroxide concentration: $c_{per}(t_l) - c_{per}(t_r)$ STEP D: Calculating a new input for the estimated concentration of hydrogen peroxide, for example taking into account the difference calculated in STEP C $$c_{per,new} = c_{per}(t_l) - ((c_{per}(t_l) - c_{per}(t_r))/2)$$

said steps B–C–D being repeated until $c_{per}(t_l)$ is equal or substantially equal $c_{per}(t_r)$ or until the difference is within a predetermined accuracy range, for example a range of $-1\%$ of $c_{per}(t_l)$ to $1\%$ $c_{per}(t_l)$.

When the system 206 controls and adjusts the pH at a value higher than 10.5, preferably at a predetermined value, the electronic device 205 calculates the hydrogen peroxide concentration (comprised between 0.5 mole/liter to 3 mole/liter) by means of the following formula, when the pH is kept constant and the sensor electrode is calibrated at the said constant value of the pH, by means of the following formula:

$$c_{per} = \left[ c_{per,cal}^{(1.5x_{cal}-0.5)} \frac{I_m}{I_{cal}} e^{0.03049(T_{cal}-T_m)} \right]^{\frac{1}{(1.5x_m-0.5)}}$$

in which $T_{cal}$, $c_{per,cal}$ and $I_{cal}$ are respectively the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

If the pH is kept constant by means of a controlling system and if the sensor electrode is not calibrated at said constant value of the pH, then the hydrogen peroxide concentration is calculated by means of the following formula:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

in which $c_{OH^-cal}$, $T_{cal}$, $c_{per,cal}$ and $I_{cal}$ are respectively the $OH^-$ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the $OH^-$ concentration of the solution of which the hydrogen peroxide concentration is to be measured;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

When the system is intended for measuring hydrogen peroxide concentrations smaller than 0.5 mole/liter in a solution having a pH higher than 10.5, the electronic device makes use of the following relationship between the factor x and the hydrogen peroxide concentration:

$$x = k \cdot c_{per}^y$$

in which x is the x factor;

k and y are constants and equal to k=0.6664 and y=−0.08055;

$c_{per}$ is the hydrogen peroxide concentration.

Inserting the said formula into the overall formula used by the electronic device, the hydrogen peroxide concentration is obtained by iterations by means of the following formula, when the sensor electrode is calibrated at the said constant value of the pH $$c_{per} = \left[ c_{per,cal}^{(1.5(kc_{per,cal}^y)-0.5)} \frac{I_m}{I_{cal}} e^{0.03049(T_{cal}-T_m)} \right]^{\frac{1}{(1.5(kc_{per}^y)-0.5)}}$$

in which $T_{cal}$, $c_{per,cal}$ and $I_{cal}$ are respectively the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$I_m$ is the output of the sensor electrode in the solution of which the hydrogen peroxide concentration is to be measured;

k and y are constant values $c_{per}$ is the hydrogen peroxide concentration of the solution of which the hydrogen peroxide concentration is to be measured.

If the temperature is kept constant by controlling said parameter and if the sensor electrode is not calibrated at said constant value of the temperature, then the hydrogen peroxide concentration is calculated by means of the following formula:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y)-0.5)}}$$

in which $c_{OH^-cal}$, $T_{cal}$, $c_{per,cal}$ and $I_{cal}$ are respectively the OH$^-$ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the OH$^-$ concentration of the solution of which the hydrogen peroxide concentration is to be measured;

$I_m$ is the output of the sensor electrode in the solution of which the hydrogen peroxide concentration is to be measured;

k and y are constant values $c_{per}$ is the hydrogen peroxide concentration of the solution of which the hydrogen peroxide concentration is to be measured.

After inserting all said elements except $c_{per}$ into the said equation, each iteration comprises the following steps:

STEP A: Inserting an estimated hydrogen peroxide concentration $c_{per}(t_r)$ into the said formula;

STEP B: Calculating by means of said formula a calculated hydrogen peroxide concentration $c_{per}(t_l)$;

STEP C: Calculating the difference between the calculated hydrogen peroxide concentration $c_{per}(t_l)$ and the estimated hydrogen peroxide concentration: $c_{per}(t_l)-c_{per}(t_r)$ STEP D: Calculating a new input for the estimated concentration of hydrogen peroxide, for example taking into account the difference calculated in STEP C $$c_{per,new}=c_{per}(t_l)-((c_{per}(t_l)-c_{per}(t_r))/2)$$

said steps B–C–D being repeated until $c_{per}(t_l)$ is equal or substantially equal $c_{per}(t_r)$ or until the difference is within a predetermined accuracy range, for example a range of −1% of $c_{per}(t_l)$ to 1% $c_{per}(t_l)$.

When the temperature regulating system controls the temperature of the solution of which the hydrogen peroxide concentration is to be measured (for example by adjusting the temperature to a specific temperature, for example 25° C. or the calibration temperature), and when the system 206 controls and adjusts the pH at a value higher than 10.5, preferably at a predetermined value (for example 12.5), the electronic device 205 calculates the hydrogen peroxide concentration (comprised between 0.5 mole/liter and 3 mole/liter) by means of the following formula, when the pH and temperature are kept constant and the sensor electrode is calibrated at the said constant values of the pH and the temperature, by means of the following formula:

$$c_{per} = \left[ c_{per,cal}^{(1.5x_{cal}-0.5)} \frac{I_m}{I_{cal}} \right]^{\frac{1}{(1.5x_m-0.5)}}$$

in which $c_{per,cal}$ and $I_{cal}$ are respectively the hydrogen peroxide concentration of the solution used for the calibration of the sensor electrode and the output of the sensor electrode in the solution used for calibration;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

If the pH and temperature are kept constant by a controlling system and if the solution is not calibrated at said constant values of the pH and/or temperature, then the hydrogen peroxide concentration is calculated by means of the following formula:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

in which $c_{OH^-cal}$, $T_{cal}$, $c_{per,cal}$ and $I_{cal}$ are respectively the OH$^-$ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the OH$^-$ concentration of the solution of which the hydrogen peroxide concentration is to be measured;

$I_m$ is the output of the sensor electrode in the solution of which the hydrogen peroxide concentration is to be measured;

$x_{cal}$ and $x_m$ are equal to about 0.53 and $c_{per}$ is the hydrogen peroxide concentration of the solution of which the hydrogen peroxide concentration is to be measured.

When the system is intended to measure hydrogen peroxide concentrations smaller than 0.5 mole/liter in a solution having a pH higher than 10.5, the electronic device makes use of the following relationship between the factor x and the hydrogen peroxide concentration:

$$x=k \cdot c_{per}^y$$

in which x is the x factor;

k and y are constants and equal to k=0.6664 and y=−0.08055;

$c_{per}$ is the hydrogen peroxide concentration.

Inserting the said formula into the overall formula used by the electronic device the hydrogen peroxide concentration is obtained by iterations by means of the following formula, when the sensor electrode is calibrated at the said constant values of the pH and temperature:

$$c_{per} = \left[ c_{per,cal}^{(1.5(kc_{per,cal}^y)-0.5)} \frac{I_m}{I_{cal}} \right]^{\frac{1}{(1.5(kc_{per}^y)-0.5)}}$$

in which $c_{per,cal}$ and $I_{cal}$ are the hydrogen peroxide concentration of the solution used for the calibration of the sensor electrode and the output of the sensor electrode in the solution used for calibration;

$I_m$ is the output of the sensor electrode of the solution of which the hydrogen peroxide concentration is to be measured;

k and y are constant values;

$c_{per}$ is the hydrogen peroxide concentration of the solution of which the hydrogen peroxide concentration is to be measured.

If the pH and temperature are kept constant by controlling said parameters and if the sensor electrode is not calibrated at said constant values of the pH and temperature, then the hydrogen peroxide concentration is calculated by means of the following formula:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y)-0.5)}}$$

in which $c_{OH^-cal}$, $T_{cal}$, $c_{per,cal}$ and $I_{cal}$ are respectively the OH⁻ concentration of the solution used for the calibration of the sensor electrode, the temperature of the solution used for the calibration of the sensor electrode, the hydrogen peroxide concentration of the solution used for the calibration of the sensor electrode and the output of the sensor electrode in the solution used for calibration;

$T_m$ is the temperature of the solution of which the hydrogen peroxide concentration is to be measured;

$c_{OH^-m}$ is the OH⁻ concentration of the solution of which the hydrogen peroxide concentration is to be measured;

$I_m$ is the output of the sensor electrode of the solution of which the hydrogen peroxide concentration is to be measured;

k and y are constant values $c_{per}$ is the hydrogen peroxide concentration of the solution of which the hydrogen peroxide concentration is to be measured.

After inserting all said elements except $c_{per}$ into the said equation, each iteration comprises the following steps:

STEP A: Inserting an estimated hydrogen peroxide concentration $c_{per}(t_r)$ into the said formula;

STEP B: Calculating by means of said formula a calculated hydrogen peroxide concentration $c_{per}(t_l)$;

STEP C: Calculating the difference between the calculated hydrogen peroxide concentration $c_{per}(t_l)$ and the estimated hydrogen peroxide concentration: $c_{per}(t_l) - c_{per}(t_r)$ STEP D: Calculating a new input for the estimated concentration of hydrogen peroxide, for example taking into account the difference calculated in STEP C $$c_{per,new} = c_{per} - ((c_{per}(t_l) - c_{per}(t_r))/2)$$

said steps B–C–D being repeated until $c_{per}(t_l)$ is equal or substantially equal $c_{per}(t_r)$ or until the difference is within a predetermined accuracy range, for example a range of −1% of $c_{per}(t_l)$ to 1% of $c_{per}(t_l)$.

The invention relates also to a method for continuous measuring of the hydrogen peroxide concentration of a solution in a range from 0.005 mole/liter to 3 mole/liter, by means of a system according to the invention. According to a first method, said method comprises the following steps:

possibly adjusting the pH at a value higher than 10.5 (when necessary);

measuring the temperature of the solution of which the hydrogen peroxide concentration is to be measured;

determining the OH⁻ concentration of the solution of which the hydrogen peroxide concentration is to be measured;

measuring the output of the sensor electrode of the solution of which the hydrogen peroxide concentration is to be measured, and calculating the hydrogen peroxide concentration of the solution of which the hydrogen peroxide concentration is to be measured by the formula:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

or by iterations using the following formula:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y)-0.5)}}$$

According to another method, the method comprises the following steps:

adjusting the pH of the solution of which the hydrogen peroxide concentration is to be measured to said predetermined value, for example the calibration pH;

adjusting the temperature of the solution of which the hydrogen peroxide concentration is to be measured to a predetermined temperature, for example the calibration temperature;

measuring the output of the sensor electrode of the solution of which the hydrogen peroxide concentration is to be measured; and calculating the hydrogen peroxide concentration of the solution of which the hydrogen peroxide concentration is to be measured by the following formula, if the calibration of the sensor electrode is performed at the said constant values for pH and temperature:

$$c_{per} = \left[ c_{per,cal}^{(1.5x_{cal}-0.5)} \frac{I_m}{I_{cal}} \right]^{\frac{1}{(1.5x_m-0.5)}}$$

and by the following formula if the said calibration is not performed at the constant values for pH and temperature:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

or by iterations using respectively:

$$c_{per} = \left[ c_{per,cal}^{(1.5(kc_{per,cal}^y)-0.5)} \frac{I_m}{I_{cal}} \right]^{\frac{1}{(1.5(kc_{per}^y)-0.5)}}$$

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y)-0.5)}}$$

When the method comprises iteration steps, the following steps are carried out:

STEP A: Inserting an estimated hydrogen peroxide concentration $c_{per}(t_r)$ into the said formula;

STEP B: Calculating by means of said formula a calculated hydrogen peroxide concentration $c_{per}(t_l)$;

STEP C: Calculating the difference between the calculated hydrogen peroxide concentration $c_{per}(t_l)$ and the estimated hydrogen peroxide concentration: $c_{per}(t_l) - c_{per}(t_r)$ STEP D: Calculating a new input for the estimated concentration of hydrogen peroxide, for example taking into account the difference calculated in STEP C $$c_{per,new} = c_{per} - ((c_{per}(t_l) - c_{per}(t_r))/2)$$

said steps B–C–D being repeated until $c_{per}(t_l)$ is equal or substantially equal $c_{per}(t_r)$ or until the difference is within a predetermined accuracy range, for example a range of −1% of $c_{per}(t_l)$ to 1% of $c_{per}(t_l)$.

Given the satisfactory working properties of the sensor, the system can be relied on to be automated. Through appropriate hard- and software, the sensor and related apparatus is capable of keeping the hydrogen peroxide concentration constant by calculating from the measured concentration how much hydrogen peroxide must be added and by driving dosage pumps.

The sensor electrode gives a stable relationship between the measured concentration and the actual hydrogen peroxide concentration so that it can quickly be established how strong the deviation is from the optimal hydrogen peroxide concentration.

FIG. 6 shows the variation of the factor "x" as a function of the hydrogen peroxide concentration. Said factor "x" has been determined experimentally by linking the output of the sensor electrode for a range of solutions containing different concentrations of hydrogen peroxide, to the real hydrogen peroxide concentrations measured by simultaneously performed titrations. As it can be seen, "x" is substantially equal to 0.53 for hydrogen peroxide concentrations higher than 0.5 mole/liter. It has been determined that, for peroxide concentrations smaller than 0.5 mole/liter in a solution having a pH higher than 10.5, the following relationship exists between the factor x and the hydrogen peroxide concentration:

$$x = k \cdot c_{per}^y$$

in which x is the x factor;

k and y are constants and equal to k=0.6664 and y=−0.08055;

$c_{per}$ is the hydrogen peroxide concentration.

FIG. 7 shows a graph of the hydrogen peroxide concentration of a solution determined by titration by means of potassium permanganate (curve A) and the hydrogen peroxide concentration determined by the system of the invention (curve B) during a period of 6 days. The decrease of the hydrogen peroxide concentration after about 10, 40 and 67 hours was obtained by dilution, while the increase after 105 hours is due to the addition of hydrogen peroxide, said variations simulating variations in a real process. As can be seen there is substantially no difference between curves A and B, i.e. the sensor electrode is working properly and is suitable for obtaining a correct measurement of the hydrogen peroxide concentration during the period of the test. The experiment was repeated after the sensor electrode had been used for two months. The same results as shown in FIG. 7 were obtained.

This shows that the sensor electrode can be used for relatively long periods of time without recalibration.

What we claim is:

1. Sensor electrode for continuously measuring a hydrogen peroxide concentration ranging from 0.05 mole/liter to 3 mole/liter, whereby said sensor electrode consists of a carbon electrode having a sensing surface for contacting a liquid medium, and whereby said sensor electrode has an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more than 0.5 mole/liter, said open circuit potential furthermore being measured with respect to a Ag/AgCl/saturated Cl⁻ reference electrode.

2. Sensor electrode according to claim 1, having an open circuit potential of −72±2 mV.

3. Sensor electrode according to claim 1, comprising a carbon element which extends between a first end and a second end, the first end contacting a copper base via the interposition of a conductive layer, said copper base and said carbon element being embedded in a resin so that the second end of the carbon element is free of resin and forms a sensing surface.

4. Sensor electrode according to claim 1, the sensing surface of which having been subjected to the following treatments:

(a) mechanical treatment comprising polishing the sensing surface successively with sandpaper, with $Al_2O_3$ polishing powder with a grit larger than 0.3 μm, and with $Al_2O_3$ polishing powder with a grit smaller than 0.3 μm, (b) cleaning by ultrasonic vibration, (c) a first electrochemical treatment of the sensor electrode in an aqueous solution having a pH between 10.5 and 14, a hydrogen peroxide concentration of more than 0.5 mole/liter, a water decomposition potential by reduction and a water decomposition potential by oxidation, the sensing surface being subjected to successive cycles of sweeping the potential of the sensor electrode between a first potential more negative than the said water decomposition potential by reduction and a second potential more positive than the said water decomposition potential by oxidation, each cycle being characterised by a current-potential curve, said first electrochemical treatment being continued until a difference of less then 1% is obtained between all data points of the current-potential curves of two successive cycles of sweeping the potential of the sensor electrode between the first potential and the second potential, (d) a second electrochemical treatment of the sensor electrode in an aqueous solution having a pH between 10.5 and 14 and a hydrogen peroxide concentration of more than 0.5 mole/liter, said second electrochemical treatment consisting of maintaining between the sensor electrode and the reference electrode a constant potential difference of +0.54V until an open circuit potential of between −65 mV and −85 mV is obtained for the sensor electrode in an alkaline solution having a pH between 10.5 and 14 and having a hydrogen peroxide concentration of more than 0.5 mole/liter.

5. System for continuously measuring a hydrogen peroxide concentration ranging from 0.5 mole/liter to 3 mole/liter of a solution having a pH higher than 10.5, said system comprising:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more than 0.5 mole/liter, said open circuit potential furthermore being measured with respect to a Ag/AgCl/saturated Cl⁻ reference electrode, said system further comprising:

(d) a temperature sensor,
(e) a second sensor, the output of which is function of the OH⁻ concentration of the liquid medium, and
(f) an electronic device, connected to the sensor electrode, the counter electrode, the reference electrode, the temperature sensor and the second sensor, whereby the electronic device calculates the hydrogen peroxide concentration by means of the following formula I:

$$c_{per} = \left[ c_{per,cal}^{(1.5 x_{cal} - 0.5)} \frac{I_m}{I_{cal}} \frac{c_{OH_{cal}^-}^{(1.5 - 0.5 x_{cal})}}{c_{OH_m^-}^{(1.5 - 0.5 x_m)}} e^{0.03049(T_{cal} - T_m)} \right]^{\frac{1}{(1.5 x_m - 0.5)}}$$

in which $c_{OH_{cal}^-}$, $T_{cal}$ and $c_{per,cal}$ are respectively the OH⁻ concentration, the temperature and the hydrogen peroxide concentration of a calibration solution used for calibrating the sensor electrode and whereby $I_{cal}$ is the output of the sensor electrode when in the calibration solution, $c_{OH_m^-}$, $T_m$ and $c_{per}$ are respectively the OH⁻ concentration, the temperature and the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53.

6. System for continuously measuring a hydrogen peroxide concentration lower than 0.5 mole/liter of a solution having a pH higher than 10.5, said system comprising:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more than 0.5 mole/liter, said open circuit potential furthermore being measured with respect to a Ag/AgCl/saturated Cl⁻ reference electrode, said system further comprising:

(d) a temperature sensor,
(e) a second sensor, the output of which is function of the OH⁻ concentration of the liquid medium, and
(f) an electronic device connected to the sensor electrode, the counter electrode, the reference electrode, the temperature sensor and the second sensor, whereby the electronic device calculates the hydrogen peroxide concentration by means of the following formula II:

$$c_{per} = \left[ c_{per,cal}^{(1.5(kc_{per,cal}^y) - 0.5)} \frac{I_m}{I_{cal}} \frac{c_{OH_{cal}^-}^{(1.5 - 0.5(kc_{per,cal}^y))}}{c_{OH_m^-}^{(1.5 - 0.5(kc_{per}^y))}} e^{0.03049(T_{cal} - T_m)} \right]^{\frac{1}{(1.5(kc_{per}^y))}}$$

in which $c_{OH_{cal}^-}$, $T_{cal}$ and $c_{per,cal}$ are respectively the OH⁻ concentration, the temperature and the hydrogen peroxide concentration in a calibration solution used for calibrating the sensor electrode and whereby $I_{cal}$ is the output of the sensor electrode when in the calibration solution, $c_{OH_m^-}$, $T_m$ and $c_{per}$ are respectively the OH⁻ concentration, the temperature and the hydrogen peroxide concentration of the solution of which the hydrogen peroxide concentration is to be measured and whereby $I_m$ is the output of the sensor electrode in the solution of which the hydrogen peroxide concentration is to be measured and k and y are constant values, whereby the electronic device calculates the hydrogen peroxide concentration in the solution by iteration, each iteration comprising the following steps:

step A: inserting an estimated hydrogen peroxide concentration $c_{per}(t_r)$ into formula II;

step B: using formula II, calculating a calculated hydrogen peroxide concentration $c_{per}(t_l)$;

step C: calculating the difference $c_{per}(t_l) - c_{per}(t_r)$ between the calculated hydrogen peroxide concentration $c_{per}(t_l)$ and the estimated hydrogen peroxide concentration $c_{per}(t_r)$;

step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$, and inserting the new estimated hydrogen peroxide concentration $c_{per}(t_r)$ into formula II;

steps B to D being repeated until the difference $c_{per}(t_l)-c_{per}(t_r)$ falls within a predetermined accuracy range.

7. System for continuously measuring a hydrogen peroxide concentration ranging from 0.5 mole/liter to 3 mole/liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said system further comprising:
(d) a temperature regulating system for controlling the temperature of the liquid medium,
(e) a sensor, the output of which is function of the OH⁻ concentration of the liquid medium, and
(f) an electronic device connected to the sensor electrode, the counter electrode, the reference electrode, and the sensor,
whereby the electronic device calculates the hydrogen peroxide concentration by means of the following formula III:

$$c_{per} = \left[c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}}\right]^{\frac{1}{(1.5x_m-0.5)}}$$

in which
$c_{OH_{cal}^-}$ and $c_{per,cal}$ are respectively the OH⁻ concentration and the hydrogen peroxide concentration of a calibration solution used for calibrating the sensor electrode and whereby $I_{cal}$ is the output of the sensor electrode when in the calibration solution, $c_{OH_m^-}$ and $c_{per}$ are respectively the OH⁻ concentration and the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53.

8. System for continuously measuring a hydrogen peroxide concentration lower than 0.5 mole/liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said system further comprising:
(d) a temperature regulating system for controlling the temperature of the liquid medium,
(e) a sensor, the output of which is function of the OH⁻ concentration of the liquid medium, and
(f) an electronic device connected to the sensor electrode, the counter electrode, the reference electrode, and the sensor,
whereby the electronic device calculates the hydrogen peroxide concentration by means of the following formula IV:

$$c_{per} = \left[c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}}\right]^{\frac{1}{(1.5(kc_{per}^y)-0.5)}}$$

in which
$c_{OH_{cal}^-}$ and $c_{per,cal}$ are respectively the OH⁻ concentration and the hydrogen peroxide concentration of a calibration solution used for calibrating the sensor electrode and whereby $I_{cal}$ is the output of the sensor electrode when in the calibration solution, $c_{OH_m^-}$ and $c_{per}$ are respectively the OH⁻ concentration and the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values,
whereby the electronic device calculates the hydrogen peroxide concentration in the solution by iteration, each iteration comprising the following steps:
step A: inserting an estimated hydrogen peroxide concentration $c_{per}(t_r)$ into formula IV,
step B: using formula IV, calculating a calculated hydrogen peroxide concentration $c_{per}(t_l)$,
step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$,
step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$ and inserting the new estimated hydrogen peroxide concentration $c_{per}(t_r)$ into formula IV, steps B to D being repeated until the difference $c_{per}(t_l)-c_{per}(t_r)$ falls within a predetermined accuracy range.

9. System for continuously measuring a hydrogen peroxide concentration ranging from 0.5 mole/liter to 3 mole/liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said system further comprising:
(d) a temperature sensor,
(e) a system for controlling and adjusting the pH of the liquid medium to a value higher than 10.5,
(f) a second sensor, the output of which is function of the OH⁻ concentration of the liquid medium,
(g) an electronic device connected to the sensor electrode, the counter electrode, the reference electrode, the temperature sensor and the second sensor, whereby the electronic device calculates the hydrogen peroxide concentration by means of the following formula V:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

in which $c_{OH_{cal}^-}$, $T_{cal}$ and $c_{per,cal}$ are respectively the OH⁻ concentration, the temperature and the hydrogen peroxide concentration of a calibration solution used for calibrating the sensor electrode and whereby $I_{cal}$ is the output of the sensor electrode when in the calibration solution, $c_{OH_m^-}$, $T_m$ and $c_{per}$ are respectively the OH⁻ concentration, the temperature and the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53.

10. System for continuously measuring a hydrogen peroxide concentration lower than 0.5 mole/liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said system further comprising:
(d) a temperature sensor,
(e) a second sensor, the output of which is function of the OH⁻ concentration of the liquid medium,
(f) a system for controlling and adjusting the pH of the liquid medium to a value higher than 10.5, and
(g) an electronic device connected to the sensor electrode, the counter electrode, the reference electrode, the temperature sensor and the second sensor, whereby the electronic device calculates the hydrogen peroxide concentration by means of the following formula VI:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y))}}$$

in which $c_{OH_{cal}^-}$, $T_{cal}$ and $c_{per,cal}$ are respectively the OH⁻ concentration, the temperature and the hydrogen peroxide concentration of a calibration solution used for calibrating the sensor electrode and whereby $I_{cal}$ is the output of the sensor electrode when in the calibration solution, $c_{OH_m^-}$, $T_m$ and $c_{per}$ are respectively the OH⁻ concentration, the temperature and the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values,
whereby the electronic device calculates the hydrogen peroxide concentration in the solution by iteration, each iteration comprising the following steps:

step A: inserting an estimated hydrogen peroxide concentration $c_{per}(t_r)$ into formula VI, step B: using formula VI, calculating a calculated hydrogen peroxide concentration $c_{per}(t_l)$, step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$, step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$ and inserting the new estimated hydrogen peroxide concentration $c_{per}(t_r)$ into formula VI, steps B to D being repeated until the difference $c_{per}(t_l)-c_{per}(t_r)$ falls within a predetermined accuracy range.

11. System for continuously measuring a hydrogen peroxide concentration ranging from 0.5 mole/liter to 3 mole/ liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said system further comprising:
(d) a temperature sensor,
(e) a system for controlling and adjusting the pH of the liquid medium to a predetermined pH value higher than 10.5, and
(f) an electronic device connected to the sensor electrode, the counter electrode, the reference electrode and the temperature sensor, whereby the electronic device calculates the hydrogen peroxide concentration by means of the following formula VII:

$$c_{per} = \left[ c_{per,cal}^{(1.5x_{cal}-0.5)} \frac{I_m}{I_{cal}} e^{0.03049(T_{cal}-T_m)} \right]^{\frac{1}{(1.5x_m-0.5)}}$$

in which $T_{cal}$ and $c_{per,cal}$ are respectively the temperature and the hydrogen peroxide concentration of a calibration solution used for calibrating the sensor electrode and whereby $I_{cal}$ is the output of the sensor electrode when in the calibration solution, and whereby the calibration solution has a pH corresponding to the said predetermined pH value, $T_m$ and $c_{per}$ are respectively the temperature and the hydrogen peroxide concentration of the solution of which the hydrogen peroxide concentration is to be measured and whereby $I_m$ is the output of the sensor electrode in the solution of which the hydrogen peroxide concentration is to be measured and $x_{cal}$ and $x_m$ are about 0.53.

12. System for continuously measuring a hydrogen peroxide concentration lower than 0.5 mole/liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/saturated Cl⁻ reference electrode, said system further comprising:
(d) a temperature sensor,
(e) a system for controlling and adjusting the pH of the liquid medium to a predetermined pH value higher than 10.5, and
(f) an electronic device connected to the sensor electrode, the counter electrode, the reference electrode and the temperature sensor,
whereby the electronic device calculates the hydrogen peroxide concentration by means of the following formula VIII $$c_{per} = \left[ c_{per,cal}^{(1.5(kc_{per,cal}^y)-0.5)} \frac{I_m}{I_{cal}} e^{0.03049(T_{cal}-T_m)} \right]^{\frac{1}{(1.5(kc_{per}^y)-0.5)}}$$

in which $T_{cal}$ and $c_{per,cal}$ are respectively the temperature and the hydrogen peroxide concentration of a calibration solution used for calibrating the sensor electrode and whereby $I_{cal}$ is the output of the sensor electrode when in the calibration solution, and whereby the calibration solution has a pH corresponding to the said predetermined pH value, $T_m$ and $c_{per}$ are respectively the temperature and the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values, whereby the electronic device calculates the hydrogen peroxide concentration in the solution by iteration, each iteration comprising the following steps:

step A: inserting an estimated hydrogen peroxide concentration $c_{per}(t_r)$ into formula VIII, step B: using formula VIII, calculating a calculated hydrogen peroxide concentration $c_{per}(t_l)$, step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$, step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$ and inserting the new estimated hydrogen peroxide concentration $c_{per}(t_r)$ into formula VIII, steps B to D being repeated until the difference until the difference $c_{per}(t_l)-c_{per}(t_r)$ falls within a predetermined accuracy range.

13. System for continuously measuring a hydrogen peroxide concentration ranging from 0.5 mole/liter to 3 mole/liter of a solution having a pH higher than 10.5, said system comprising:
(a) a sensor electrode,
(b) a counter electrode and
(c) a reference electrode,
whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/saturated Cl⁻ reference electrode, said system further comprising:
(d) a temperature regulating system for controlling the temperature of the liquid medium at a predetermined temperature,
(e) a system for controlling and adjusting the pH of the liquid medium to a predetermined pH value higher than 10.5,
(f) an electronic device connected to the sensor electrode, the counter electrode and the reference electrode,
whereby the electronic device calculates the hydrogen peroxide concentration by means of the following formula IX:

$$c_{per} = \left[ c_{per,cal}^{(1.5x_{cal}-0.5)} \frac{I_m}{I_{cal}} \right]^{\frac{1}{(1.5x_m-0.5)}}$$

in which $c_{per,cal}$ is the hydrogen peroxide concentration of a calibration solution used for calibrating the sensor electrode and whereby $I_{cal}$ is the output of the sensor electrode when in the calibration solution, and whereby the temperature of the calibration solution is the said predetermined temperature and whereby the pH of the calibration solution corresponds to the said predetermined pH value, $c_{per}$ is the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53.

14. System for continuously measuring a hydrogen peroxide concentration lower than 0.5 mole/liter of a solution having a pH higher than 10.5, said system comprising:
(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/saturated Cl⁻ reference electrode, said system further comprising:
(d) a temperature regulating system for controlling the temperature of the liquid medium at a predetermined temperature,
(e) a system for controlling and adjusting the pH of the liquid medium to a predetermined pH value higher than 10.5,
(f) an electronic device connected to the sensor electrode, the counter electrode and the reference electrode, whereby the electronic device calculates the hydrogen peroxide concentration by means of the following formula X:

$$c_{per} = \left[ c_{per,cal}^{(1.5(kc_{per,cal}^y)-0.5)} \frac{I_m}{I_{cal}} \right]^{\frac{1}{(1.5(kc_{per}^y)-0.5)}}$$

in which $c_{per,cal}$ is the hydrogen peroxide concentration of a calibration solution used for calibrating the sensor electrode and whereby $I_{cal}$ is the output of the sensor electrode when in the calibration solution, and whereby the temperature of the calibration solution is the said predetermined temperature and whereby the pH of the calibration solution corresponds to the said predetermined pH value, $c_{per}$ is the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values, whereby the electronic device calculates the hydrogen peroxide concentration in the solution by iteration, each iteration comprising the following steps:

step A: inserting an estimated hydrogen peroxide concentration $c_{per}(t_i)$ into formula X, step B: using formula X, calculating a calculated hydrogen peroxide concentration $c_{per}(t_l)$, step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$, step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$ and inserting the new estimated hydrogen peroxide concentration $c_{per}(t_r)$ into formula X, steps B to D being repeated until the difference $c_{per}(t_l)-c_{per}(t_r)$ falls within a predetermined accuracy range.

15. Method for continuously measuring a hydrogen peroxide concentration ranging from 0.5 mole/liter to 3 mole/liter of a solution having a pH higher than 10.5, said method comprising using:
(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more than 0.5 mole/liter, said open circuit potential furthermore being measured with respect to a Ag/AgCl/saturated Cl⁻ reference electrode, said method further using:
(d) a temperature sensor,
(e) a second sensor, the output of which is function of the OH⁻ concentration of the liquid medium,
(f) a system for controlling and adjusting the pH of the liquid medium at a value higher than 10.5, and
(g) an electronic device connected to the sensor electrode, the counter electrode, the reference electrode, the temperature sensor and the second sensor, said electronic device calculating the hydrogen peroxide concentration by means of the following formula I:

$$c_{per} = \left[ c_{per,cal}^{(1.5x_{cal}-0.5)} \frac{I_m}{I_{cal}} \frac{c_{OH_{cal}^-}^{(1.5-0.5x_{cal})}}{c_{OH_m^-}^{(1.5-0.5x_m)}} e^{0.03049(T_{cal}-T_m)} \right]^{\frac{1}{(1.5x_m-0.5)}}$$

in which $c_{OH_{cal}^-}$, $T_{cal}$ and $c_{per,cal}$ are respectively the OH⁻ concentration, the temperature and the hydrogen peroxide concentration of a calibration solution used for calibrating the sensor electrode and whereby $I_{cal}$ is the output of the sensor electrode when in the calibration solution, $c_{OH_m^-}$, $T_m$ and $c_{per}$ are respectively the OH⁻ concentration, the temperature and the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53, the said method comprising the following steps:

measuring the temperature $T_m$ of the solution of which the hydrogen peroxide concentration is to be measured, determining the OH⁻ concentration $c_{OH_m^-}$ of the solution of which the hydrogen peroxide concentration is to be measured, measuring the output $I_m$ of the sensor electrode when in the solution of which the hydrogen peroxide concentration is to be measured, calculating the said hydrogen peroxide concentration $c_{per}$ using formula I.

16. Method for continuously measuring a hydrogen peroxide concentration lower than 0.5 mole/liter of a solution having a pH higher than 10.5, said method comprising using:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said method further using:

(d) a temperature sensor,
(e) a second sensor, the output of which is function of the OH⁻ concentration of the liquid medium,
(f) a system for controlling and adjusting the pH of the liquid medium at a value higher than 10.5, and
(g) an electronic device connected to the sensor electrode, the counter electrode, the reference electrode, the temperature sensor and the second sensor, whereby the electronic device calculates the hydrogen peroxide concentration by means of the following formula II:

$$c_{per} = \left[ c_{per,cal}^{(1.5(kc_{per,cal}^y)-0.5)} \frac{I_m}{I_{cal}} \frac{c_{OH_{cal}^-}^{(1.5-0.5(kc_{per,cal}^y))}}{c_{OH_m^-}^{(1.5-0.5(kc_{per}^y))}} e^{0.03049(T_{cal}-T_m)} \right]^{\frac{1}{(1.5(kc_{per}^y))}}$$

in which $c_{OH_{cal}^-}$, $T_{cal}$ and $c_{per,cal}$ are respectively the OH⁻ concentration, the temperature and the hydrogen peroxide concentration of a calibration solution used for calibrating the sensor electrode and whereby $I_{cal}$ is the output of the sensor electrode when in the calibration solution, $c_{OH_m^-}$, $T_m$ and $c_{per}$ are respectively the OH⁻ concentration, the temperature and the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values, said electronic device calculating the hydrogen peroxide concentration in the solution by iteration, each iteration comprising the following steps:

step A: inserting an estimated hydrogen peroxide concentration $c_{per}(t_r)$ into formula II;
step B: using formula II, calculating a calculated hydrogen peroxide concentration $c_{per}(t_l)$;
step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$;
step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$, and inserting the new estimated hydrogen peroxide concentration $c_{per}(t_r)$ into formula II steps B to D being repeated until the difference $c_{per}(t_l)-c_{per}(t_r)$ falls within a predetermined accuracy range, the said method comprising the following steps:

measuring the temperature $T_m$ of the solution of which the hydrogen peroxide concentration is to be measured, determining the OH⁻ concentration $c_{OH_m^-}$ of the solution of which the hydrogen peroxide concentration is to be measured, measuring the output $I_m$ of the sensor electrode when in the solution of which the hydrogen peroxide concentration is to be measured, calculating the hydrogen peroxide concentration $c_{per}$ using iterations of formula II.

17. Method for continuously measuring a hydrogen peroxide concentration ranging from 0.5 mole/liter to 3 mole/ liter of a solution having a pH higher than 10.5, said method comprising using:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said method further using:

(d) a temperature sensor,
(e) a system for controlling and adjusting the pH of the liquid medium at a predetermined value higher than 10.5, and
(f) an electronic device connected to the sensor electrode, the counter electrode, the reference electrode and the temperature sensor, said electronic device calculating the hydrogen peroxide concentration by means of the following formula VII:

$$c_{per} = \left[ c_{per,cal}^{(1.5x_{cal}-0.5)} \frac{I_m}{I_{cal}} e^{0.03049(T_{cal}-T_m)} \right]^{\frac{1}{(1.5x_m-0.5)}}$$

in which $T_{cal}$ and $c_{per,cal}$ are respectively the temperature and the hydrogen peroxide concentration of a calibration solution used for calibrating the sensor electrode and whereby $I_{cal}$ is the output of the sensor electrode when in the calibration solution, the pH of the calibration solution corresponding to the said predetermined pH value, $T_m$ and $c_{per}$ are respectively the temperature and the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53, the said method comprising the following steps:

adjusting the pH of the solution of which the hydrogen peroxide concentration is to be measured to the predetermined pH value, measuring the temperature $T_m$ of the solution of which the hydrogen peroxide concentration is to be measured, measuring the output $I_m$ of the sensor electrode when in the solution of which the hydrogen peroxide concentration is to be measured, calculating the said hydrogen peroxide concentration $c_{per}$ using formula VII.

18. Method for continuously measuring the hydrogen peroxide concentration lower than 0.5 mole/liter of a solution having a pH higher than 10.5, said method comprising using:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said method further using:

(d) a temperature sensor,
(e) a system for controlling and adjusting the pH of the liquid medium at a value higher than 10.5, and
(f) an electronic device connected to the sensor electrode, the counter electrode, the reference electrode and the temperature sensor, whereby the electronic device calculates the hydrogen peroxide concentration by means of the following formula VIII:

$$c_{per} = \left[ c_{per,cal}^{(1.5(kc_{per,cal}^y)-0.5)} \frac{I_m}{I_{cal}} e^{0.03049(T_{cal}-T_m)} \right]^{\frac{1}{(1.5(kc_{per}^y)-0.5)}}$$

in which $T_{cal}$ and $c_{per,cal}$ are respectively the temperature and the hydrogen peroxide concentration of a calibration solution used for calibrating the sensor electrode and whereby $I_{cal}$ is the output of the sensor electrode when in the calibration solution, $T_m$ and $c_{per}$ are respectively the temperature and the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values, said electronic device calculating the hydrogen peroxide concentration in the solution by iteration, each iteration comprising the following steps:

step A: inserting an estimated hydrogen peroxide concentration $c_{per}(t_r)$ into formula VIII, step B: using formula VII, calculating a calculated hydrogen peroxide concentration $c_{per}(t_l)$, step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$, step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$, and inserting the new estimated hydrogen peroxide concentration $c_{per}(t_r)$ into formula VIII steps B to D being repeated until the difference $c_{per}(t_l)-c_{per}(t_r)$ falls within a predetermined accuracy range, the said method comprising the following steps:

adjusting the pH of the solution of which the hydrogen peroxide concentration is to be measured to the predetermined pH value, measuring the temperature $T_m$ of the solution of which the hydrogen peroxide concentration is to be measured, measuring the output $I_m$ of the sensor electrode when in the solution of which the hydrogen peroxide concentration is to be measured, calculating the hydrogen peroxide concentration $c_{per}$ using iterations of formula VIII.

19. Method for continuously measuring a hydrogen peroxide concentration ranging from 0.5 mole/liter to 3 mole/liter of a solution having a pH higher than 10.5, said method comprising using:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said method further using:

(d) a temperature regulating system for controlling the temperature of the liquid medium at a predetermined temperature level,
(e) a system for controlling and adjusting the pH of the liquid medium at a predetermined value higher than 10.5, and
(f) an electronic device connected to the sensor electrode, the counter electrode and the reference electrode, said electronic device calculating the hydrogen peroxide concentration by means of the following formula IX:

$$c_{per} = \left[ c_{per,cal}^{(1.5x_{cal}-0.5)} \frac{I_m}{I_{cal}} \right]^{\frac{1}{(1.5x_m-0.5)}}$$

in which $c_{per,cal}$ is the hydrogen peroxide concentration of a calibration solution used for calibrating the sensor electrode and whereby $I_{cal}$ is the output of the sensor electrode when in the calibration solution, the calibration solution having a temperature corresponding to the predetermined temperature level and a pH corresponding to the said predetermined pH value, $c_{per}$ is the hydrogen peroxide concentration of the solution of which the hydrogen peroxide concentration is to be measured and whereby $I_m$ is the output of the sensor electrode in the solution of which the hydrogen peroxide concentration is to be measured, and $x_{cal}$ and $x_m$ are about 0.53, the said method comprising the following steps:

adjusting the pH of the solution of which the hydrogen peroxide concentration is to be measured to the predetermined pH value, adjusting the temperature of the solution of which the hydrogen peroxide concentration is to be measured to the predetermined temperature level, measuring the output $I_m$ of the sensor electrode when in the solution of which the hydrogen peroxide concentration is to be measured, calculating the said hydrogen peroxide concentration $c_{per}$ using formula IX.

20. Method for continuously measuring the hydrogen peroxide concentration lower than 0.5 mole/liter of a solution having a pH higher than 10.5, said method comprising using:

(a) a sensor electrode,
(b) a counter electrode and
(c) a reference electrode, whereby the sensor electrode is a carbon electrode having a sensing surface for contacting a liquid medium, said sensor electrode having an open circuit potential with a mean value between −65 mV and −85 mV, the fluctuation margin of the open circuit potential, once established, being less than 2 mV with respect to the said mean value, said open circuit potential being measured in an alkaline solution having a pH between 10.5 and 14 and having a hydrogen peroxide concentration of more 0.5 mole/liter, said open circuit potential furthermore being measured with respect to a Ag/AgCl/ saturated Cl⁻ reference electrode, said method further using:

(d) a temperature regulating system for controlling the temperature of the liquid medium at a predetermined temperature level,
(e) a system for controlling and adjusting the pH of the liquid medium at a predetermined value higher than 10.5, and
(f) an electronic device connected to the sensor electrode, the counter electrode and the reference electrode, whereby the electronic device calculates the hydrogen peroxide concentration by means of the following formula X:

$$c_{per} = \left[ c_{per,cal}^{(1.5(kc_{per,cal}^y)-0.5)} \frac{I_m}{I_{cal}} \right]^{\frac{1}{(1.5(kc_{per}^y)-0.5)}}$$

in which $c_{per,cal}$ is the hydrogen peroxide concentration of a calibration solution used for calibrating the sensor electrode and whereby $I_{cal}$ is the output of the sensor electrode when in the calibration solution, $c_{per}$ is the hydrogen peroxide concentration of the solution of which the hydrogen peroxide concentration is to be measured and whereby $I_m$ is the output of the sensor electrode in the solution of which the hydrogen peroxide concentration is to be measured, and k and y are constant values, said electronic device calculating the hydrogen peroxide concentration in the solution by iteration, each iteration comprising the following steps:

step A: inserting an estimated hydrogen peroxide concentration $c_{per}(t_r)$ into formula X, step B: using formula X, calculating a calculated hydrogen peroxide concentration $c_{per}(t_l)$, step C: calculating the difference $c_{per}(t_l)-c_{per}(t_r)$ between the calculated hydrogen peroxide concentration $c_{per}(t_l)$ and the estimated hydrogen peroxide concentration $c_{per}(t_r)$, step D: calculating a new estimated hydrogen peroxide concentration $c_{per}(t_r)$ on the basis of the calculated hydrogen peroxide concentration $c_{per}(t_l)$ and the difference $c_{per}(t_l)-c_{per}(t_r)$, and inserting the new estimated hydrogen peroxide concentration $c_{per}(t_r)$ into formula X, steps B to D being repeated until the difference $c_{per}(t_l)-c_{per}(t_r)$ falls within a predetermined accuracy range, the said method comprising the following steps:

adjusting the pH of the solution of which the hydrogen peroxide concentration is to be measured to the predetermined pH value, adjusting the temperature of the solution of which the hydrogen peroxide concentration is to be measured to the predetermined temperature level, measuring the output $I_m$ of the sensor electrode when in the solution of which the hydrogen peroxide concentration is to be measured, calculating the hydrogen peroxide concentration $c_{per}$ using iterations of formula X.

* * * * *